US007079889B2

(12) United States Patent  
Nakada

(10) Patent No.: US 7,079,889 B2  
(45) Date of Patent: Jul. 18, 2006

(54) LIVING BODY IMPEDANCE MEASUREMENT APPARATUS

(75) Inventor: Masato Nakada, Tokyo (JP)

(73) Assignee: Tanita Corporation, Tokyo (JP)

( * ) Notice: Subject to any disclaimer, the term of this patent is extended or adjusted under 35 U.S.C. 154(b) by 428 days.

(21) Appl. No.: 10/609,555

(22) Filed: Jul. 1, 2003

(65) Prior Publication Data

US 2004/0010205 A1  Jan. 15, 2004

(30) Foreign Application Priority Data

Jul. 11, 2002  (JP)  ............................. 2002-202843

(51) Int. Cl.  
*A61B 5/00* (2006.01)

(52) U.S. Cl. .................................................. 600/547

(58) Field of Classification Search .................... None  
See application file for complete search history.

(56) References Cited

U.S. PATENT DOCUMENTS

| | | | | | |
|---|---|---|---|---|---|
| 3,149,627 | A | * | 9/1964 | Bagno | 600/506 |
| 3,994,284 | A | * | 11/1976 | Voelker | 600/506 |
| 4,947,862 | A | * | 8/1990 | Kelly | 600/547 |
| 5,335,667 | A | * | 8/1994 | Cha et al. | 600/547 |
| 5,611,351 | A | * | 3/1997 | Sato et al. | 600/547 |
| 5,899,922 | A | * | 5/1999 | Loos | 607/2 |
| 6,253,103 | B1 | * | 6/2001 | Baura | 600/547 |
| 6,336,045 | B1 | * | 1/2002 | Brooks | 600/547 |
| 6,516,222 | B1 | * | 2/2003 | Fukuda | 600/547 |
| 6,567,692 | B1 | * | 5/2003 | Kohashi et al. | 600/547 |
| 2002/0062090 | A1 | | 5/2002 | Chai et al. | |
| 2004/0167423 | A1 | * | 8/2004 | Pillon et al. | 600/547 |

FOREIGN PATENT DOCUMENTS

| | | | |
|---|---|---|---|
| EP | 1 219 238 A1 | | 7/2002 |
| JP | 4158839 | * | 6/1992 |
| JP | 2835656 | | 10/1998 |

OTHER PUBLICATIONS

C.E.B. Neves and M.n. Souza, A Comparison Between Impedance Measured by a Commercial Analyzer and Your Value Adjusted by a Theoretical Model in Body Composition Evaluation, Oct. 25-28, 2001 International Conference of the IEEE, vol. 4, pp. 3388-3391.*

* cited by examiner

*Primary Examiner*—Max Hindenburg  
*Assistant Examiner*—Kristin D. Rogers  
(74) *Attorney, Agent, or Firm*—McDermott Will & Emery LLP

(57) ABSTRACT

A living body impedance measurement apparatus is provided which measures a voltage attributed to the impedance of a living body, and separates it into a voltage attributed to a resistance component and a voltage attributed to a reactance component. Then, the voltage attributed to the resistance component, the voltage attributed to the reactance component, and resistance and reactance components of an impedance of an external reference unit are substituted into an impedance calculation formula that accounts for impedance fluctuation. A fluctuation constant is thereby calculated that is a constant for a fluctuation variable representing fluctuation caused by impedance change factors. The resistance component and the reactance component of a true impedance of the living body are then calculated based on the fluctuation constant and the measured living body impedance.

3 Claims, 5 Drawing Sheets

LIVING BODY IMPEDANCE MEASUREMENT APPARATUS

BACKGROUND OF THE INVENTION

1. Field of the Invention

The present invention relates to a living body impedance measurement apparatus in which actually measured living body impedance is separated into resistance component and reactance component in order to provide the true impedance of the living body.

2. Prior Art

An impedance measurement method has been developed (see Japanese Patent No. 2835656) wherein a set of several reference resistors each having the predetermined resistance to properly divide the measured living body impedance is provided in a current supplying path in series with a living body for measuring the impedance thereof, then, voltage drop across each of the reference resistors and voltage drop across the living body are measured; thereafter, based on the resistance values of the reference resistors and the corresponding voltage values measured thereacross a correlation formula for correlating therebetween is determined; and the living body impedance is calculated by the determined correlation formula, depending on the voltage measured across the living body.

Unfortunately, such previous impedance measurement method entails presence of some impedance change factors in a sinusoidal wave generator for producing constant current, a voltage/current converter, and a current supplying path, for example. Therefore, the previous measurement method is defective in that the living body impedance resulted from the measurement and calculation process is frequently lack of precision.

In view of the above it is an object of the present invention to solve the problem in the prior art as described above and to provide an improved living body impedance measurement apparatus having capability of measurement with higher precision and having less effect on the measurement by any fluctuation which may be caused due to presence of any impedance change factors.

SUMMARY OF THE INVENTION

In order to attain such object the present invention provides a living body impedance measurement apparatus, comprising: a voltage measurement unit; a separation unit; a calculation formula storage unit; a fluctuation constant calculation unit; a fluctuation constant storage unit; and a living body impedance calculation unit, wherein said voltage measurement unit measures a voltage attributed to an impedance of a living body or an external reference unit, or of a living body, an external reference unit or an internal reference unit, said separation unit separates the voltage attributed to the impedance as measured by said measurement unit into a voltage attributed to its resistance component and a voltage attributed to its reactance component, said calculation formula storage unit stores an impedance calculation formula therein in advance, said impedance calculation formula correlates a true impedance variable representing resistance component and reactance component of true impedance of the living body or the external reference unit with a fluctuation variable representing a fluctuation which may be caused in said voltage measurement unit due to any impedance change factor as well as a measured voltage variable representing the voltage attributed to resistance component and the voltage attributed to reactance component of an actually measured impedance, said fluctuation constant calculation unit calculates a fluctuation constant that is the constant for the fluctuation variable by substituting the voltage attributed to resistance component and the voltage attributed to reactance component, which are separated from each other by said separation unit, corresponding to the voltage attributed to the impedance of the external reference unit as measured by the voltage measurement unit, as well as the resistance component and the reactance component of the impedance of the external reference unit as measured by the voltage measurement unit for terms in said impedance calculation formula stored in said calculation formula storage unit in advance, said fluctuation constant storage unit stores the fluctuation constant calculated by said fluctuation constant calculation unit, and said living body impedance calculation unit calculates the resistance component and the reactance component of the true living body impedance by substituting the fluctuation constant stored in the fluctuation constant storage unit and the voltage attributed to the living body impedance as measured by the voltage measurement unit for the terms in said impedance calculation formula stored in said calculation formula storage unit in advance.

According to one embodiment of the present invention the fluctuation constant calculation unit calculates a fluctuation constant that is the constant for the fluctuation variable by substituting each voltage attributed to each resistance component and each voltage attributed to each reactance component, which are separated from each other by said separation unit, corresponding to each voltage attributed to each impedance of each of a plurality of different external reference units as measured by the voltage measurement unit, as well as each resistance component and each reactance component of each impedance of each of a plurality of different external reference units as measured by the voltage measurement unit for the terms in said impedance calculation formula stored in said calculation formula storage unit in advance.

According to another embodiment of the present invention the impedance calculation formula includes:

fluctuation variables: "$C_R$" representing any fluctuation based on the scale factor and the phase of resistance component; "$C_X$" representing any fluctuation based on the scale factor and the phase of reactance component; "$V_{OSR}$" representing any fluctuation based on the offset voltage to resistance component axis; and "$V_{OSX}$" representing any fluctuation based on the offset voltage to reactance component axis;

measured voltage variables: "$V_{BR}$" representing the voltage attributed to resistance component of the living body or the external reference unit; "$V_{BX}$" representing the voltage attributed to reactance component; "$V_{RR}$" representing the voltage attributed to resistance component of the internal reference unit; and "$V_{RX}$" representing the voltage attributed to reactance component; and true impedance component variables: "$R_B$" representing resistance component of the true impedance of the living body or the external reference unit; and "$X_B$" representing reactance component of that true impedance, and said impedance calculation formula is written as follows:

$$\begin{pmatrix} R_B \\ X_B \end{pmatrix} = \begin{pmatrix} C_R \\ C_X \end{pmatrix} \times \frac{\begin{pmatrix} V_{BR} \\ V_{BX} \end{pmatrix} - \begin{pmatrix} V_{OSR} \\ V_{OSX} \end{pmatrix}}{\begin{pmatrix} V_{RR} \\ V_{RX} \end{pmatrix} - \begin{pmatrix} V_{OSR} \\ V_{OSX} \end{pmatrix}}.$$

BRIEF DESCRIPTION OF THE DRAWINGS

Now, the present invention will be described in more detail with reference to the accompanying drawings in which.

DESCRIPTION OF THE PREFERRED EMBODIMENTS

First of all, reference is made to a first embodiment of the present invention wherein some hardware approach is used to separate actually measured living body impedance into resistance component and reactance component for deriving true impedance of the living body.

Figure 1:
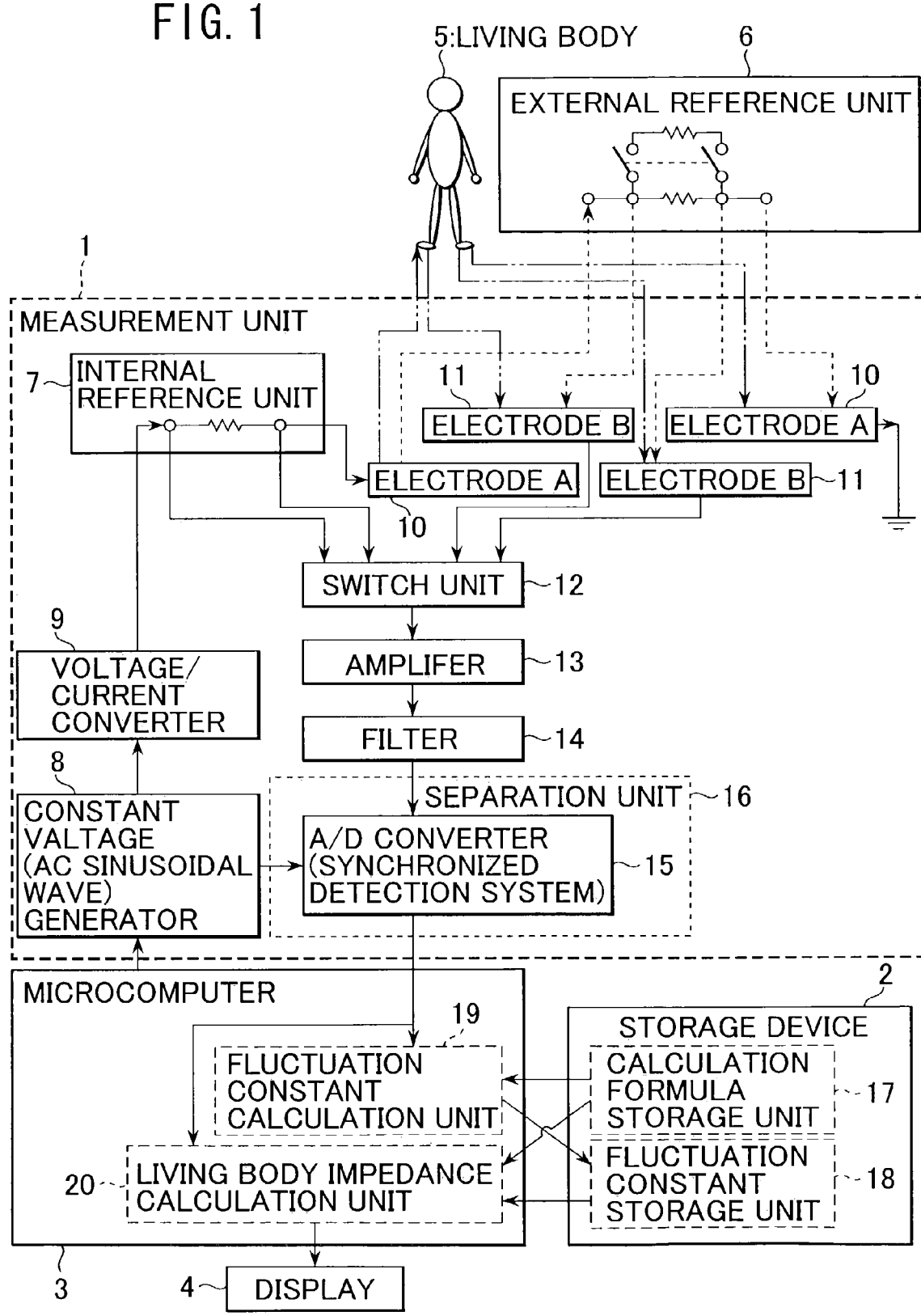
FIG. 1 is a block diagram of a living body impedance measurement apparatus according to a first embodiment of the present invention.

Referring to FIG. 1, a living body impedance measurement apparatus constructed in accordance with the first embodiment of the present invention is illustrated in the form of block diagram.

The living body impedance measurement apparatus according to the first embodiment comprises a measurement unit 1, a storage device 2, a microcomputer 3 and a display unit 4.

The measurement unit 1 is configured to measure the voltage attributed to impedance of a living body 5 or an external reference unit 6 or an internal reference unit 7. The measurement unit 1 comprises a constant voltage (AC sinusoidal wave) generator 8, a voltage/current converter 9, the internal reference unit 7, electrodes A 10, electrodes B 11, a switch unit 12, an amplifier 13, a filter 14, and an A/D converter (a synchronized detection system) 15.

The constant voltage (AC sinusoidal wave) generator 8 is operated to produce a constant voltage at higher frequency (at 50 KHz, for example) which is output to the voltage/current converter 9, and to produce a sinusoidal wave generation timing signal which is output to the A/D converter (a synchronized detection system) 15. The voltage/current converter 9 converts the constant voltage from the constant voltage (AC sinusoidal wave) generator 8 into a constant current which is output to the internal reference unit 7.

The internal reference unit 7 provides reference impedance for compensating any effect on the impedance by any fluctuation in constant current from the constant voltage (AC sinusoidal wave) generator 8 and the voltage/current converter 9 due to presence of any change in circumstance, such as temperature variation, etc. The internal reference unit 7 includes a set of reference resistors each having predetermined resistance for use in the impedance measurement method (see Japanese Patent No. 2835656) as described above regarding the prior art. In this embodiment a single resistor having predetermined resistance is used for the internal reference unit 7.

The electrodes A 10 are used for applying the constant current fed through the internal reference unit 7 from the voltage/current converter 9 to the living body 5 or the external reference unit 6. The electrodes B 11 are used for detecting the voltage developed across the living body 5 or the external reference unit 6.

The switch unit 12 is connected to switch between the voltage developed across the internal reference unit 7 as the result of the constant current fed therethrough and the voltage developed between two electrodes B 11 as the result of the constant current fed through the living body 5 or the external reference unit 6 therebetween.

The amplifier 13 functions to amplify the voltage fed through the switch unit 12, which is attributed to the impedance of the internal reference unit 7 or to the impedance of the living body 5 or the external reference unit 6. The filter 14 is provided to filter out any noise component of the voltage signal amplified by the amplifier 13.

The A/D converter (the synchronized detection system) 15 functions to convert the (analogue) voltage signal from which any noise component is removed by the filter 14 into a digital signal, and to separate it into a voltage attributed to resistance component and a voltage attributed to reactance component of the internal reference unit 7 or of the living body 5 or the external reference unit 6 according to the sinusoidal wave generation timing signal from the constant voltage (AC sinusoidal wave) generator 8. Then, they are output to the microcomputer 3. In this connection, it is to be noted that the A/D converter (the synchronized detection system) 15 forms not only a part of the measurement unit 1, but also a separation unit 16 for separating the voltage attributed to the impedance as measured by the measurement unit 1 into the voltage attributed to resistance component and the voltage attributed to reactance component.

The storage device 2 comprising a calculation formula storage unit 17 and a fluctuation constant storage unit 18 provides a temporarily storage function and other well known storage functions when various calculations are performed. An EEPROM is used for the storage device 2.

The calculation formula storage unit 17 stores an impedance calculation formula therein in advance, and the impedance calculation formula correlates a true impedance variable representing resistance component and reactance component of true impedance of the living body or the external reference unit with a fluctuation variable representing any fluctuation which may be caused due to any impedance change factor in said measurement unit 1 and a measured voltage variable representing the voltage attributed to resistance component and the voltage attributed to reactance component of actually measured impedance.

Figure 2:
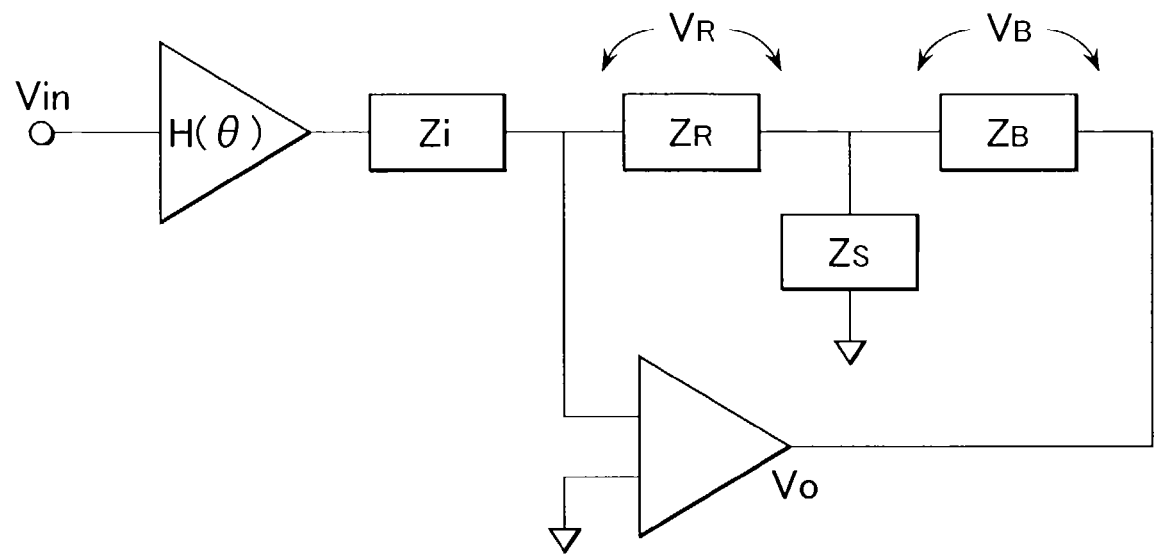
FIG. 2 is a view illustrating a circuit model in a measurement unit.

The impedance calculation formula (1) written below is derived from a circuit model in the measurement unit 1 as shown in FIG. 2, taking into account of any fluctuation which may be caused due to any impedance change factor in the measurement unit 1. In FIG. 2, "H(θ)" is phase shift component in the measurement unit 1, "Zi" is impedance of the voltage/current converter 9, "$Z_R$" is impedance of internal reference unit 7, "$Z_S$" is impedance due to any stray capacitance and the like, "$Z_B$" is impedance of the living body 5 or the external reference unit 6, "$V_0$" is voltage across the internal reference unit 7 and the living body 5 (or the external reference unit 6), "$V_R$" is voltage across the impedance component of the internal reference unit 7, and "$V_B$" is voltage across the impedance component of the living body 5 or the external reference unit 6.

According to this circuit model the impedance $Z_B$ of the living body 5 or the external reference unit 6 is written as follows:

$$Z_B = V_B(1 - Z_R/Z_S)Z_R/V_R = CV_B/V_R$$

where "C" is a fluctuation variable representing any fluctuation depending on the scale factor and the phase. Then, a fluctuation variable "$V_{OS}$" representing any fluctuation based on the offset voltage mainly attributed to "$Z_S$" is incorporated into this formula, and each of the variables is divided into resistance component and reactance component. More particularly, "$Z_B$" is divided into "$R_B$": true impedance component variable representing resistance component of the true impedance for the living body 5 or the external reference unit 6 and "$X_B$": true impedance component variable representing reactance component of that true impedance; "C" is divided into "$C_R$": a fluctuation variable representing any fluctuation based on the scale factor and the phase of resistance component and "$C_X$": a fluctuation variable representing any fluctuation based on the scale factor and the phase of reactance component; "$V_B$" is divided into "$V_{BR}$": a measured voltage variable representing the voltage attributed to resistance component for the living body 5 or the external reference unit 6 and "$V_{BX}$": a measured voltage variable representing the voltage attributed to reactance component; "$V_R$" is divided into "$V_{RR}$": a measured voltage variable representing the voltage attributed to resistance component for the internal reference unit 7 and "$V_{RX}$": a measured voltage variable representing the voltage attributed to reactance component; and "$V_{OS}$" is divided into "$V_{OSR}$": a fluctuation variable representing any fluctuation based on the offset voltage to resistance component axis and "$V_{OSX}$": a fluctuation variable representing any fluctuation based on the offset voltage to reactance component axis. As the result, the following formula is derived:

$$\begin{pmatrix} R_B \\ X_B \end{pmatrix} = \begin{pmatrix} C_R \\ C_X \end{pmatrix} \times \frac{\begin{pmatrix} V_{BR} \\ V_{BX} \end{pmatrix} - \begin{pmatrix} V_{OSR} \\ V_{OSX} \end{pmatrix}}{\begin{pmatrix} V_{RR} \\ V_{RX} \end{pmatrix} - \begin{pmatrix} V_{OSR} \\ V_{OSX} \end{pmatrix}} \quad (1)$$

In the above formula the fluctuation variables "$C_R$" and "$C_X$" each representing fluctuation based on the scale factor and the phase as well as the fluctuation variables "$V_{OSR}$" and "$V_{OSX}$" each representing fluctuation based on the offset voltage correspond to the fluctuation variables each representing fluctuation which may be caused due to any impedance change factor in the measurement unit 1.

Figure 3:
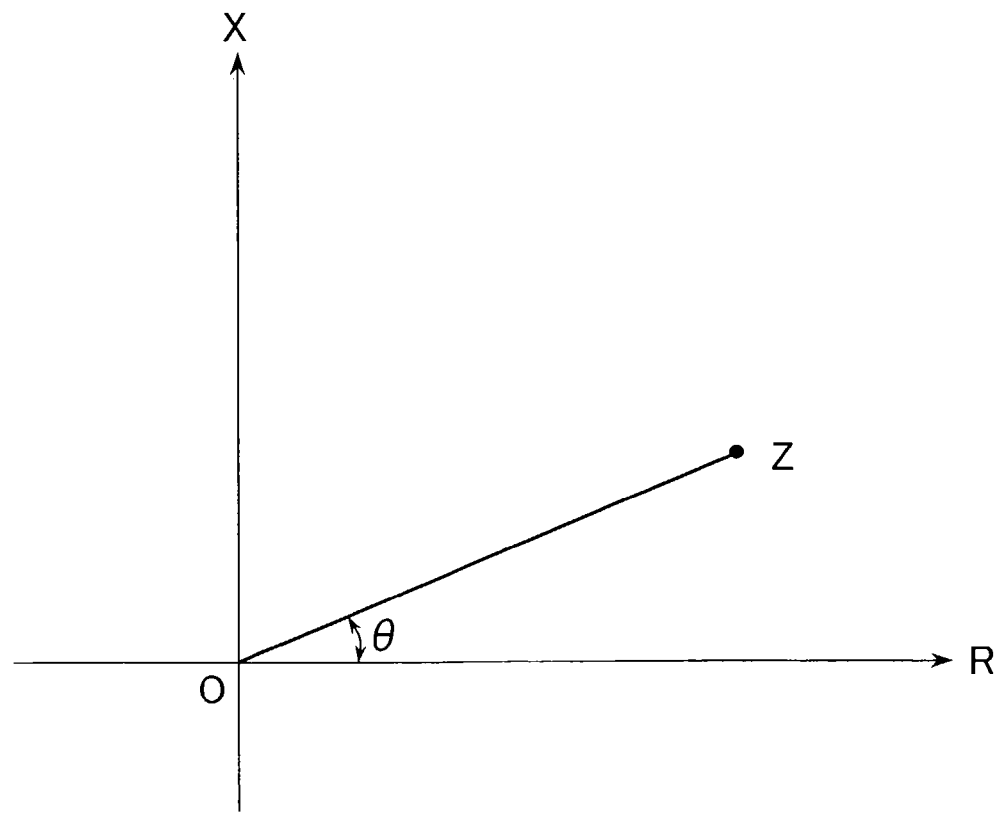
FIG. 3 is a view showing the relationship between resistance component and reactance component of impedance in a coordinate.

FIG. 3 is a graph showing the relationship between resistance and reactance components of the impedance in a coordinate. The vertical axis "X" of the coordinate represents the reactance component and the horizontal axis "R" represents the resistance component. A point "Z" represents the impedance, an origin "O" in the coordinate represents "zero" point, and a deflection angle "θ" represents any phase difference. The fluctuation variables "$C_R$" and "$C_X$" each representing fluctuation based on the scale factor and the phase are those that represent any fluctuation in the direction of a line OZ and any fluctuation in deflection angle θ. The fluctuation variables "$V_{OSR}$" and "$V_{OSX}$" each representing fluctuation based on the offset voltage are those that represent any shift of the origin O in the coordinate.

The fluctuation constant storage unit 18 stores the fluctuation constant calculated by a fluctuation constant calculation unit 19 that is described in more detail hereafter.

The microcomputer 3 comprises the fluctuation constant calculation unit 19 and a living body impedance calculation unit 20, and the microcomputer 3 provides a control function of controlling generation of higher frequency constant voltage by the constant voltage (AC sinusoidal wave) generator 8 and other well known control functions.

The fluctuation constant calculation unit 19 calculates a fluctuation constant that is the constant for the fluctuation variable by substituting the voltage attributed to resistance component and the voltage attributed to reactance component, which are sent by the A/D converter (the synchronized detection system) 15 after the measurement using the internal reference unit 7 and the external reference unit 6, as well as the known resistance component and the known reactance component of the impedance of the external reference unit 6 as measured by the measurement unit 1 for the terms in said impedance calculation formula (1) stored in said storage unit in advance, and then, sends the calculated fluctuation constant to the fluctuation constant storage unit 18.

The living body impedance calculation unit 20 calculates the resistance component and the reactance component of the true impedance of the living body 5 by substituting the fluctuation constant stored in the fluctuation constant storage unit 18 as well as the voltage attributed to resistance component and the voltage attributed to reactance component of the impedance of the living body 5 as measured by the measurement unit 1 for the terms in said impedance calculation formula (1) stored in the calculation formula storage unit 17.

The display unit 4 displays the result of calculation provided by the living body impedance calculation unit 20.

Figure 4:
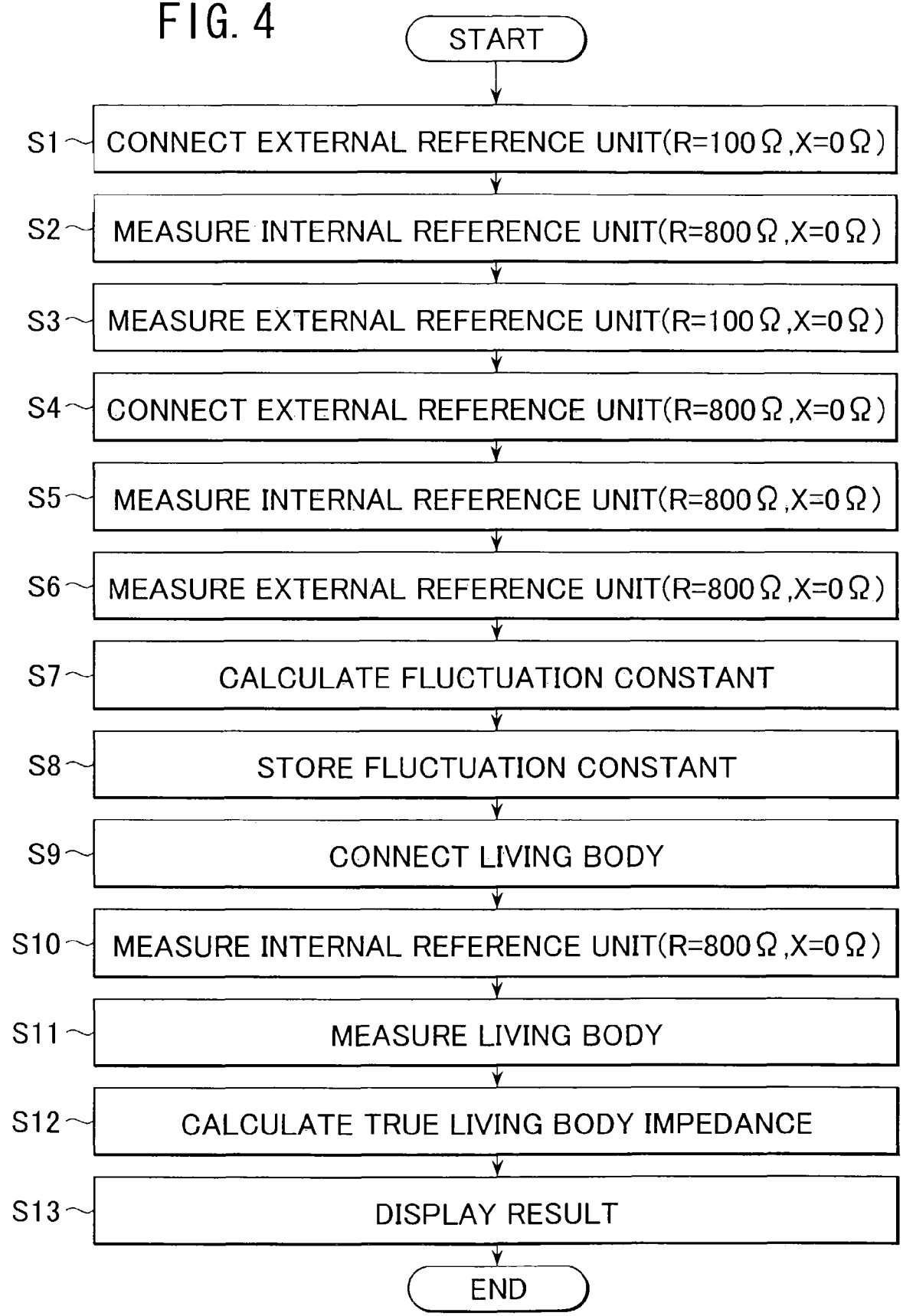
FIG. 4 is a flow chart illustrating an operation procedure for the living body impedance measurement apparatus.

Now, an operation of the living body impedance measurement apparatus according to the first embodiment of the present invention will be described with reference to a flow chart in FIG. 4.

At step S1, the external reference unit 6 having the known impedance (e.g. R=100 Ω, X=0 Ω) corresponding to the lower limit of the living body impedance measurement range is connected to the electrode A 10 and the electrode B 11, as shown in FIG. 1.

Then, under the control of the microcomputer 3 the constant voltage (AC sinusoidal wave) generator 8 produces and sends a constant voltage at high frequency (at 50 KHz, for example) to the voltage/current converter 9. Then, the converter 9 converts the high frequency constant voltage into a constant current that is output to the internal reference unit 7. The constant voltage (AC sinusoidal wave) generator 8 also produce a sinusoidal wave generation timing signal which is output to the A/D converter (the synchronized detection system) 15. The internal reference unit 7 having the known impedance (e.g. R=800 Ω, X=0 Ω) is connected in circuit by the switch unit 12 for detecting the voltage developed across the internal reference unit 7. Then, the amplifier 13 amplifies the voltage and the filter 14 filters out any noise included in the amplified voltage. Next, the A/D converter (the synchronized detection system) 15 converts the voltage (in the form of analogue) into a digital voltage and separates it into the voltage attributed to resistance component and the voltage attributed to reactance component of the internal reference unit 7 according to the sinusoidal wave generation timing signal from the constant voltage (AC sinusoidal wave) generator 8. The separated voltages are sent to the microcomputer 3 which then transfers them to the storage device 2 wherein the voltage attributed to resistance component and the voltage attributed to reactance component of the internal reference unit 7 are temporarily stored (at step S2).

Thereafter, the switch unit 12 is operated to connect the external reference unit 6, instead of the internal reference unit 7, for detecting the voltage developed across the external reference unit 6. Then, the amplifier 13 amplifies the voltage and the filter 14 filters out any noise included in the amplified voltage. Next, the A/D converter (the synchronized detection system) 15 converts the voltage (in the form of analogue) into a digital voltage and separates it into the voltage attributed to resistance component and the voltage attributed to reactance component of the external reference unit 6 according to the sinusoidal wave generation timing signal from the constant voltage (AC sinusoidal wave) generator 8. The separated voltages are sent to the microcomputer 3 which then transfers them to the storage device 2 wherein the voltage attributed to resistance component and the voltage attributed to reactance component of the external reference unit 6 are temporarily stored (at step S3).

As described above, the external reference unit 6 having the known impedance (e.g. R=100 Ω, X=0 Ω) corresponding to the lower limit of the living body impedance measurement range is connected to the electrode A 10 and the electrode B 11. Now, the external reference unit 6 is replace with another one having the known impedance (e.g. R=800 Ω, X=0 Ω) corresponding to the upper limit of the living body impedance measurement range (at step S4).

Thereafter, the process equivalent to step S2 as above is performed so that the voltage attributed to resistance component and the voltage attributed to reactance component of the internal reference unit 7 are temporarily stored in the storage device 2 (at step S5).

Then, the process equivalent to step S3 as above is performed so that the voltage attributed to resistance component and the voltage attributed to reactance component of the external reference unit 6 having the known impedance (e.g. R=800 Ω, X=0 Ω) corresponding to the upper limit of the living body impedance measurement range are temporarily stored in the storage device 2 (at step S6).

Next, in the fluctuation constant calculation unit 19, the voltage attributed to resistance component and the voltage attributed to reactance component as temporarily stored in the storage device 2 at step S3 as well as the resistance component and the reactance component of the impedance of the external reference unit 6 connected to the electrodes A 10 and B 11 at step S1 are substituted for the terms in the formula (1) as above to produce a "First Equation". More particularly, the voltage attributed to the resistance component (R=800 Ω) of the internal reference unit 7 (R=800 Ω, X=0 Ω) at the time when the external reference unit 6 (R=100 Ω, X=0 Ω) is connected is substituted for the term of measured voltage variable "$V_{RR}$" in the formula (1). The voltage attributed to the reactance component (X=0 Ω) of the internal reference unit 7 (R=800 Ω, X=0 Ω) at the time the external reference unit 6 (R=100 Ω, X=0 Ω) is connected is substituted for the measured voltage variable "$V_{RX}$" in the formula (1). The voltage attributed to the resistance component (R=100 Ω) of the external reference unit 6 (R=100 Ω, X=0 Ω) at the time it is connected is substituted for the measured voltage variable "$V_{BR}$" in the formula (1). The voltage attributed to the reactance component (X=0 Ω) of the external reference unit 6 (R=100 Ω, X=0 Ω) at the time it is connected is substituted for the measured voltage variable "$V_{BX}$" in the formula (1). The resistance component (R=100 Ω) of the external reference unit 6 (R=100 Ω, X=0 Ω) at the time it is connected is substituted for the true impedance component variable "$R_B$" in the formula (1). And, the reactance component (X=0 Ω) of the external reference unit 6 (R=100 Ω, X=0 Ω) at the time it is connected is substituted for the true impedance component variable "$X_B$" in the formula (1). In such manner, the "First Equation" is resulted.

Next, the voltage attributed to resistance component and the voltage attributed to reactance component as temporarily stored in the storage device 2 at step S6 as well as the resistance component and the reactance component of the impedance of the external reference unit 6 connected to the electrodes A 10 and B 11 at step S4 are substituted for the terms in the formula (1) as above to produce a "Second Equation". More particularly, the voltage attributed to the resistance component (R=800 Ω) of the internal reference unit 7 (R=800 Ω, X=0 Ω) at the time when the external reference unit 6 (R=800 Ω, X=0 Ω) is connected is substituted for the term of measured voltage variable "$V_{RR}$" in the formula (1). The voltage attributed to the reactance component (X=0 Ω) of the internal reference unit 7 (R=800 Ω, X=0 Ω) at the time the external reference unit 6 (R=800 Ω, X=0 Ω) is connected is substituted for the measured voltage variable "$V_{RX}$" in the formula (1). The voltage attributed to the resistance component (R=800 Ω) of the external reference unit 6 (R=800 Ω, X=0 Ω) at the time it is connected is substituted for the measured voltage variable "$V_{BR}$" in the formula (1). The voltage attributed to the reactance component (X=0 Ω) of the external reference unit 6 (R=800 Ω, X=0 Ω) at the time it is connected is substituted for the measured voltage variable "$V_{BX}$" in the formula (1). The resistance component (R=800 Ω) of the external reference unit 6 (R=800 Ω, X=0 Ω) at the time it is connected is substituted for the true impedance component variable "$R_B$" in the formula (1). And, the reactance component (X=0 Ω) of the external reference unit 6 (R=800 Ω, X=0 Ω) at the time it is connected is substituted for the true impedance component variable "$X_B$" in the formula (1). In such manner, the "Second Equation" is resulted.

The First and Second Equations are solved as the simultaneous equations to derive the constants (the fluctuation constants) for the fluctuation variables "$C_R$" and "$C_X$" as well as those for the measured voltage variables "$V_{OSR}$" and "$V_{OSX}$" (at step S7).

The fluctuation constant storage unit 18 permanently stores the fluctuation constants derived in such manner (at step S8). At this point, the voltage attributed to resistance component and the voltage attributed to reactance component as temporarily stored in the storage device 2 may be deleted.

Then, a part of the living body 5 is connected to the electrodes A 10 and B 11, as shown in FIG. 1 (at step 9).

Next, the process equivalent to step S2 as above is performed so that the voltage attributed to resistance component and the voltage attributed to reactance component of the internal reference unit 7 are temporarily stored in the storage device 2 (at step S10).

Thereafter, the switch unit 12 is operated to connect the living body 5, instead of the internal reference unit 7, for detecting the voltage developed across the living body 5. Then, the amplifier 13 amplifies the voltage and the filter 14 filters out any noise included in the amplified voltage. Next, the A/D converter (the synchronized detection system) 15 converts the voltage (in the form of analogue) into a digital voltage and separates it into the voltage attributed to resistance component and the voltage attributed to reactance component of the living body 5 according to the sinusoidal wave generation timing signal from the constant voltage (AC sinusoidal wave) generator 8. The separated voltages are then sent to the living body impedance calculation unit 20 in the microcomputer 3 (at step S11).

Thereafter, in the living body impedance calculation unit 20, the voltage attributed to resistance component and the voltage attributed to reactance component of the living body 5 produced in such manner as well as the fluctuation constants stored in the fluctuation constant storage unit 18 are substituted for the terms in the formula (1) stored in the calculation formula storage unit 17 in order to derive the resistance component "$R_B$" and the reactance component "$X_B$" of the true impedance of the living body 5. More particularly, the voltage attributed to the resistance component of the living body 5 as separated by the A/D converter (the synchronized detection system) 15 is substituted for the measured voltage variable "$V_{BR}$" in the formula (1). The voltage attributed to the reactance component of the living body 5 is substituted for the measured voltage variable "$V_{BX}$" in the formula (1). The voltage attributed to the resistance component of the internal reference unit 7 as temporarily stored in the storage device 2 at step S11 is substituted for the measured voltage variable "$V_{RR}$" in the formula (1). The voltage attributed to the reactance component of the internal reference unit 7 is substituted for the measured voltage variable "$V_{RX}$" in the formula (1). Each of fluctuation constants stored in the fluctuation constant storage unit 18 at step S8 is substituted for the fluctuation variables "$C_R$" and "$C_X$" in the formula (1). Furthermore, each of fluctuation constants for compensating the offset voltage is substituted for the fluctuation variables "$V_{OSR}$" and "$V_{OSX}$" in the formula (1). As the result, the resistance component "$R_B$" and the reactance component "$X_B$" of the true impedance of the living body 5 are derived (at step S12).

Finally, the display unit 4 displays the resistance component "$R_B$" and the reactance component "$X_B$" of the true impedance of the living body 5 as derived by the living body impedance calculation unit 20 (at step S13). Then, a sequence of process steps is terminated.

Now, reference is made to a second embodiment of the present invention wherein some software approach is used to separate actually measured living body impedance into resistance component and reactance component for deriving true impedance of the living body.

Figure 5:
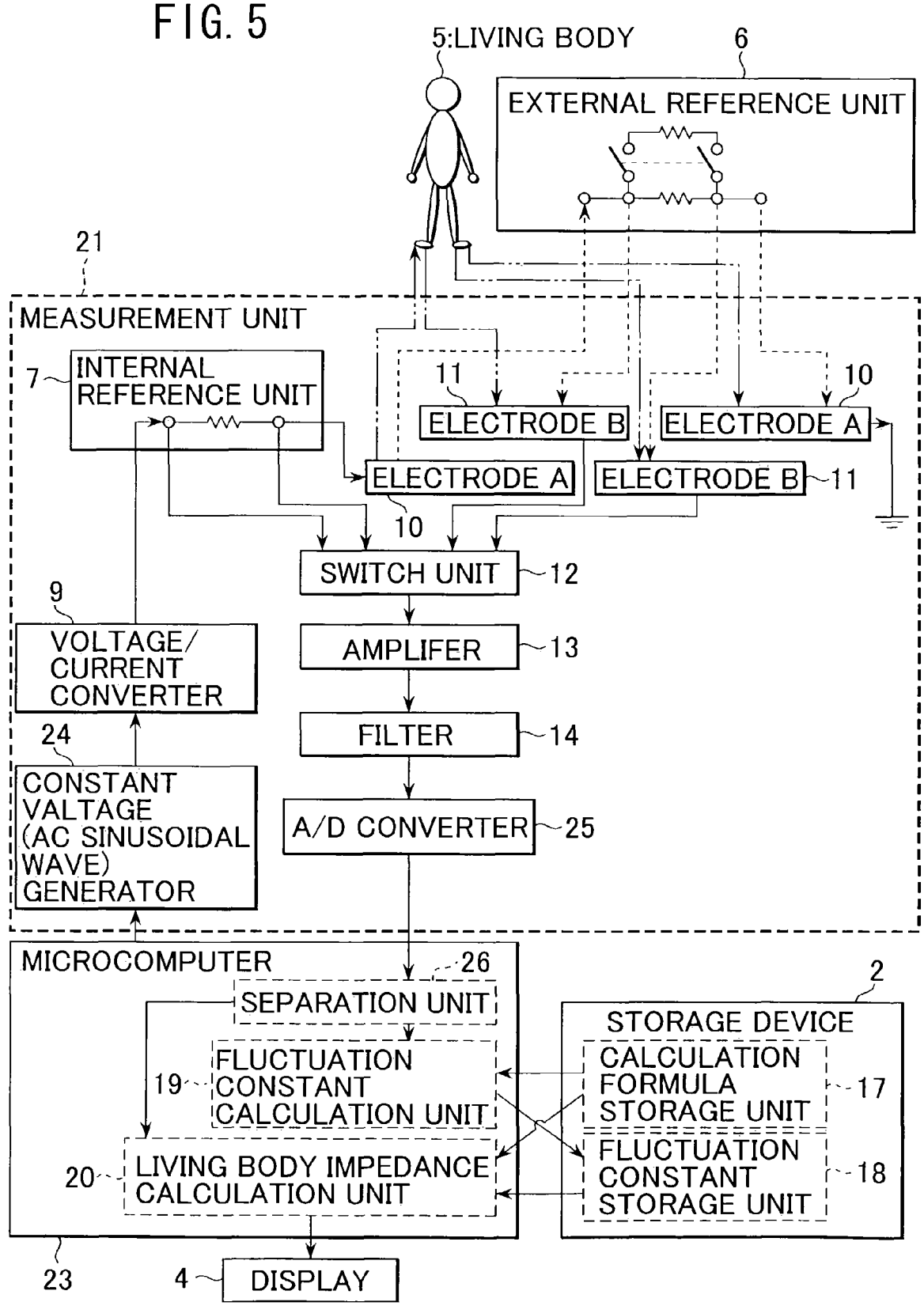
FIG. 5 a block diagram of a living body impedance measurement apparatus according to a second embodiment of the present invention.

Referring to FIG. 5, a living body impedance measurement apparatus constructed in accordance with the second embodiment of the present invention is illustrated in the form of block diagram.

The living body impedance measurement apparatus according to the second embodiment comprises a measurement unit 21, a storage device 2, a microcomputer 23 and a display unit 4.

The measurement unit 21 is configured to measure the voltage attributed to impedance of a living body 5 or an external reference unit 6 or an internal reference unit 7. The measurement unit 21 comprises a constant voltage (AC sinusoidal wave) generator 24, a voltage/current converter 9, the internal reference unit 7, electrodes A 10, electrodes B 11, a switch unit 12, an amplifier 13, a filter 14, and an A/D converter 25. Detailed description of the voltage/current converter 9, the internal reference unit 7, the electrodes A 10, the electrodes B 11, the switch unit 12, the amplifier 13 and the filter 14 is omitted, here, because they are same as those of the first embodiment as described above. Only the constant voltage (AC sinusoidal wave) generator 24 and the A/D converter 25 will be described, here.

The constant voltage (AC sinusoidal wave) generator 24 generates a constant voltage at high frequency (at 50 KHz, for example) which is output to the voltage/current converter 9. (But, it generates no sinusoidal wave generation timing signal which is output to the A/D converter, as in the first embodiment.)

The A/D converter 25 converts the (analogue) voltage signal from which any noise component is removed by the filter 14 into a digital signal which is output to the microcomputer 23. (But, it provides no separation function of separating the voltage attributed to the impedance into a voltage attributed to resistance component and a voltage attributed to reactance component, as in the first embodiment.)

Detailed description of the storage device 2 (comprising a calculation formula storage unit 17 and a fluctuation constant storage unit 18) is omitted, here, because it is same as that of the first embodiment.

The microcomputer 23 comprises a separation unit 26, a fluctuation constant calculation unit 19 and a living body impedance calculation unit 20, and the microcomputer 23 provides a control function of controlling generation of high frequency constant voltage by the constant voltage (AC sinusoidal wave) generator 24 and other well known control functions.

The separation unit 26 is configured to calculate the voltage attributed to resistance component and the voltage attributed to reactance component of actually measured impedance of the internal reference unit 7 or the living body 5 or the external reference unit 6, based on the voltage attributed to the impedance provided by the A/D converter 25 and an amplitude of time division of a period that is same as or advanced by 90° to that of sinusoidal wave generated by the constant voltage generator 24.

The fluctuation constant calculation unit 19 calculates a fluctuation constant that is the constant for the fluctuation variable by substituting the voltage attributed to resistance component and the voltage attributed to reactance component, which are separated from each other by the arithmetic operation of the separation unit 26 after measurement using the internal reference unit 7 and the external reference unit 6, as well as the known resistance component and the known reactance component of the impedance of the external reference unit 6 as measured by the measurement unit 21 for the terms in said impedance calculation formula (1) stored in said calculation formula storage unit 17 in advance The living body impedance calculation unit 20 calculates the resistance component and the reactance component of the true impedance of the living body 5 by substituting the fluctuation constant stored in the fluctuation constant storage unit 18 as well as the voltage attributed to resistance component and the voltage attributed to reactance component of the impedance of the living body 5, which are separated from each other by the separation unit 26 after measurement by the measurement unit 21, for the terms in said impedance calculation formula (1) stored in the calculation formula storage unit 17 in advance.

The display unit 4 displays the result of calculation provided by the living body impedance calculation unit 20.

Now, an operation of the living body impedance measurement apparatus according to the second embodiment of the present invention will be described with reference to a flow chart in FIG. 4.

At step S1, the external reference unit 6 having the known impedance (e.g. R=100 Ω, X=0 Ω) corresponding to the lower limit of the living body impedance measurement range is connected to the electrode A 10 and the electrode B 11, as shown in FIG. 5.

Then, under the control of the microcomputer 23 the constant voltage (AC sinusoidal wave) generator 24 produces and sends a constant voltage at high frequency (at 50 KHz, for example) to the voltage/current converter 9. Then, the converter 9 converts the high frequency constant voltage into a constant current that is output to the internal reference unit 7. Then, the internal reference unit 7 having the known impedance (e.g. R=800 Ω, X=0 Ω) is connected in circuit by the switch unit 12 for detecting the voltage developed across the internal reference unit 7. Then, the amplifier 13 amplifies the voltage and the filter 14 filters out any noise included in the amplified voltage. Next, the A/D converter 25 converts the voltage (in the form of analogue) into a digital voltage which is output to the separation unit 26 in the microcomputer 23.

Figure 6:
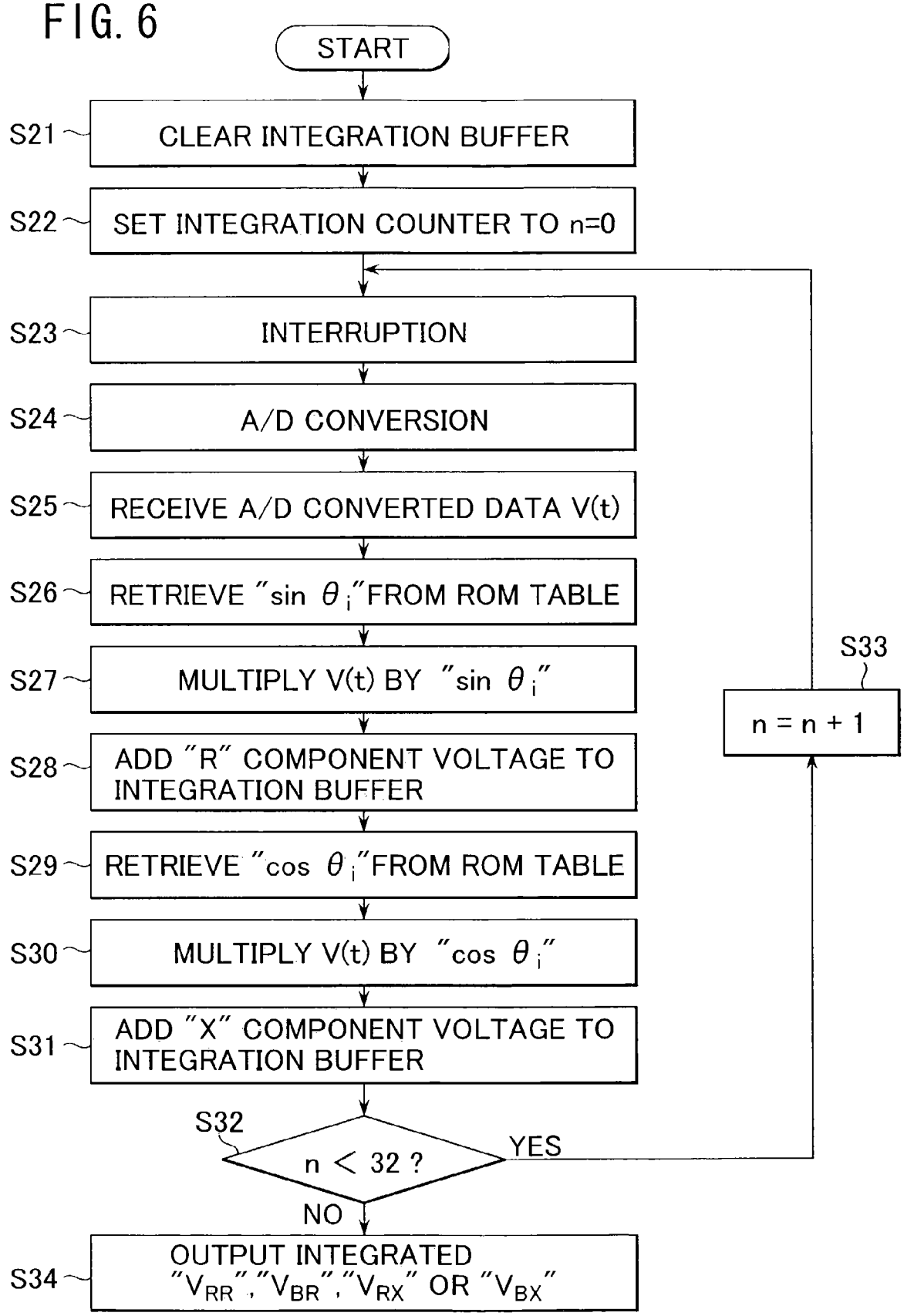
FIG. 6 is a flow chart illustrating an operation procedure for a separation unit in the apparatus according to the second embodiment.

Next, at step S2, the separation unit 26 in the microcomputer 23 calculates the voltage attributed to resistance component and the voltage attributed to the reactance component of actually measured impedance of the internal reference unit 7 according to a flow chart in FIG. 6.

Now, the process performed at step S2 and illustrated in FIG. 6 will be described in more detail. Each of integration buffers for "R" component voltage and "X" component voltage in the separation unit 26 is cleared (at step S21). An integration counter in the separation unit 26 is set to "n=0" (at step S22). An interruption occurs (at step S23), and thereafter, an operation of the A/D converter 25 is performed (at step S24). The A/D converter 25 produces a digital signal of voltage attributed to the impedance (V(t)) which is fed into the separation unit (at step S25). Then, an amplitude (sin $\theta_1$) of time division of a period that is same as that of sinusoidal wave generated by the constant voltage (AC sinusoidal wave) generator 24 is retrieved from a ROM table in the microcomputer 23 (at step S26). Next, the voltage (V(t)) attributed to the measured impedance of the internal reference unit 7, which is fed from the A/D converter 25, is multiplied by the amplitude (sin $\theta_1$) of time division of a period that is same as that of sinusoidal wave generated by the constant voltage (AC sinusoidal wave) generator 24, which is retrieved from a ROM table in the microcomputer 23 (at step S27). The resulting product is added to the "R" component voltage integration buffer (at step S28). Then, an amplitude (cos $\theta_1$) of time division of a period that is advanced by 90° to that of sinusoidal wave generated by the constant voltage (AC sinusoidal wave) generator 24 is retrieved from the ROM table in the microcomputer 23 (at step S29). Thereafter, the voltage (V(t)) attributed to the measured impedance of the internal reference unit 7, which is fed from the A/D converter 25, is multiplied by the amplitude (cos $\theta_1$) of time division of a period that is advanced by 90° to that of sinusoidal wave generated by the constant voltage (AC sinusoidal wave) generator 24, which is retrieved from the ROM table in the microcomputer 23 (at step S30). The resulting product is added to the "X" component voltage integration buffer (at step S31). Then, assuming that the integration counter is "n<32" (or an answer of step S32 is "YES"), the counter is incremented by one (n=n+1) (at step S33). The routine returns to step S23 for repeating the process. In this connection, it is noted that "i" in the amplitude "sin $\theta_i$" and "cos $\theta_i$" is incremented by one at steps S26 and S29. On the other hand, if the integration counter is not less than "32" (or an answer of step S32 is "NO"), the measured voltage variables "$V_{RR}$" and "$V_{RX}$" integrated in the "R" and "X" composition voltage integration buffers are temporarily stored in the storage device 2 (at step S34).

Next, the switch unit 12 is operated to connect the external reference unit 6 (R=100 Ω, X=0 Ω), instead of the internal reference unit 7, for detecting the voltage developed across the external reference unit 6. Then, the amplifier 13 amplifies the voltage and the filter 14 filters out any noise included in the amplified voltage. Next, the A/D converter 25 converts the voltage (in the form of analogue) into a digital voltage which is fed to the separation unit 26 in the microcomputer 23 (at step S3).

Next, at step S3, the separation unit 26 in the microcomputer 23 calculates the voltage attributed to resistance component and the voltage attributed to the reactance component of actually measured impedance of the external reference unit 6 according to the flow chart in FIG. 6.

Now, the process performed at step S3 and illustrated in FIG. 6 will be described in more detail. Each of the integration buffers for "R" component voltage and "X" component voltage in the separation unit 26 is cleared (at step S21). The integration counter in the separation unit 26 is set to "n=0" (at step S22). An interruption occurs (at step S23), and thereafter, an operation of the A/D converter 25 is performed (at step S24). The A/D converter 25 produces a digital signal of voltage attributed to the impedance (V(t)) which is fed into the separation unit (at step S25). Then, an amplitude (sin $\theta_1$) of time division of a period that is same as that of sinusoidal wave generated by the constant voltage (AC sinusoidal wave) generator 24 is retrieved from the ROM table in the microcomputer 23 (at step S26). Next, the voltage (V(t)) attributed to the measured impedance of the external reference unit 6, which is fed from the A/D converter 25, is multiplied by the amplitude (sin $\theta_1$) of time division of a period that is same as that of sinusoidal wave generated by the constant voltage (AC sinusoidal wave) generator 24, which is retrieved from a ROM table in the microcomputer 23 (at step S27). The resulting product is added to the "R" component voltage integration buffer (at step S28). Then, an amplitude (cos $\theta_1$) of time division of a period that is advanced by 90° to that of sinusoidal wave generated by the constant voltage (AC sinusoidal wave) generator 24 is retrieved from the ROM table in the microcomputer 23 (at step S29). Thereafter, the voltage (V(t)) attributed to the measured impedance of the external reference unit 6, which is fed from the AID converter 25, is multiplied by the amplitude. (cos $\theta_1$) of time division of a period that is advanced by 90° to that of sinusoidal wave generated by the constant voltage (AC sinusoidal wave) generator 24, which is retrieved from the ROM table in the microcomputer 23 (at step S30). The resulting product is added to the "X" component voltage integration buffer (at step S31). Then, assuming that the integration counter is "n<32" (or an answer of step S32 is "YES"), the counter is incremented by one (n=n+1) (at step S33). The routine returns to step S23 for repeating the process. In this connection, it is noted that "i" in the amplitude "sin $\theta_i$" and "cos $\theta_i$" is incremented by one at steps S26 and S29. On the other hand, if the integration counter is not less than "32" (or an answer of step S32 is "NO"), the measured voltage variables "$V_{BR}$" and "$V_{BX}$" integrated in the "R" and "X" composition voltage integration buffers are temporarily stored in the storage device 2 (at step S34).

As described above, the external reference unit 6 having the known impedance (e.g. R=100 Ω, X=0 Ω) corresponding to the lower limit of the living body impedance measurement range is connected to the electrode A 10 and the electrode B 11. Now, the external reference unit 6 is replace with another one having the known impedance (e.g. R=800 Ω, X=0 Ω) corresponding to the upper limit of the living body impedance measurement range (at step S4).

Thereafter, the process equivalent to step S2 as above is performed so that the voltage attributed to resistance component and the voltage attributed to reactance component of the internal reference unit 7 are temporarily stored in the storage device 2 (at step S5).

Then, the process equivalent to step S3 as above is performed so that the voltage attributed to resistance component and the voltage attributed to reactance component of the external reference unit 6 having the known impedance (e.g. R=800 Ω, X=0 Ω) corresponding to the upper limit of the living body impedance measurement range are temporarily stored in the storage device 2 (at step S6).

Then, detailed description of steps S7 to S9 is omitted because they are substantially same as those of the first embodiment as described above.

Next, the process equivalent to step S2 as above is performed so that the voltage attributed to resistance component and the voltage attributed to reactance component of the internal reference unit 7 are temporarily stored in the storage device 2 (at step S10).

Thereafter, the switch unit 12 is operated to connect the living body 5, instead of the internal reference unit 7, for detecting the voltage developed across the living body 5. Then, the amplifier 13 amplifies the voltage and the filter 14 filters out any noise included in the amplified voltage. Next, the A/D converter 25 converts the voltage (in the form of analogue) into a digital voltage which is then fed to the separation unit 26 in the microcomputer 23.

Next, the separation unit 26 in the microcomputer 23 calculates the voltage attributed to resistance component and the voltage attributed to the reactance component of actually measured impedance of the living body 5 according to a flow chart in FIG. 6 (at step S11).

Now, the process performed at step S11 and illustrated in FIG. 6 will be described in more detail. Each of the integration buffers for "R" component voltage and "X" component voltage in the separation unit 26 is cleared (at step S21). The integration counter in the separation unit 26 is set to "n=0" (at step S22). An interruption occurs (at step S23), and thereafter, an operation of the A/D converter 25 is performed (at step S24). The A/D converter 25 produces a digital signal of voltage attributed to the impedance (V(t)) which is fed into the separation unit (at step S25). Then, an amplitude (sin $\theta_1$) of time division of a period that is same as that of sinusoidal wave generated by the constant voltage (AC sinusoidal wave) generator 24 is retrieved from the ROM table in the microcomputer 23 (at step S26). Next, the voltage (V(t)) attributed to the measured impedance of the living body 5, which is fed from the A/D converter 25, is multiplied by the amplitude (sin $\theta_1$) of time division of a period that is same as that of sinusoidal wave generated by the constant voltage (AC sinusoidal wave) generator 24, which is retrieved from the ROM table in the microcomputer 23 (at step S27). The resulting product is added to the "R" component voltage integration buffer (at step S28). Then, an amplitude (cos $\theta_1$) of time division of a period that is advanced by 90° to that of sinusoidal wave generated by the constant voltage (AC sinusoidal wave) generator 24 is retrieved from the ROM table in the microcomputer 23 (at step S29). Thereafter, the voltage (V(t)) attributed to the measured impedance of the living body 5, which is fed from the A/D converter 25, is multiplied by the amplitude (cos $\theta_1$) of time division of a period that is advanced by 90° to that of sinusoidal wave generated by the constant voltage (AC sinusoidal wave) generator 24, which is retrieved from the ROM table in the microcomputer 23 (at step S30). The resulting product is added to the "X" component voltage integration buffer (at step S31). Then, assuming that the integration counter is "n<32" (or an answer of step S32 is "YES"), the counter is incremented by one (n=n+1) (at step S33). The routine returns to step S23 for repeating the process. In this connection, it is noted that "i" in the amplitude "sin $\theta_i$" and "cos $\theta_i$" is incremented by one at steps S26 and S29. On the other hand, if the integration counter is not less than "32" (or an answer of step S32 is "NO"), the measured voltage variables "$V_{BR}$" and "$V_{BX}$" integrated in the "R" and "X" composition voltage integration buffers are sent to the living body impedance calculation unit 20 (at step S34).

Thereafter, in the living body impedance calculation unit 20, the voltage attributed to resistance component and the voltage attributed to reactance component of the living body 5 produced in such manner as well as the fluctuation constants stored in the fluctuation constant storage unit 18 are substituted for the terms in the formula (1) stored in the calculation formula storage unit 17 in order to derive the resistance component "$R_B$" and the reactance component "$X_B$" of the true impedance of the living body 5. More particularly, the voltage attributed to the resistance component of the living body 5 as separated by the separator unit 26 is substituted for the measured voltage variable "$V_{BR}$" in the formula (1). The voltage attributed to the reactance component of the living body 5 is substituted for the measured voltage variable "$V_{BX}$" in the formula (1). The voltage attributed to the resistance component of the internal reference unit 7 as temporarily stored in the storage device 2 at step S11 is substituted for the measured voltage variable "$V_{RR}$" in the formula (1). The voltage attributed to the reactance component of the internal reference unit 7 is substituted for the measured voltage variable "$V_{RX}$" in the formula (1). Each of fluctuation constants stored in the fluctuation constant storage unit 18 at step S8 is substituted for the fluctuation variables "$C_R$" and "$C_X$" in the formula (1). Furthermore, each of fluctuation constants for compensating the offset voltage is substituted for the fluctuation variables "$V_{OSR}$" and "$V_{OSX}$" in the formula (1). As the result, the resistance component "$R_B$" and the reactance component "$X_B$" of the true impedance of the living body 5 are derived (at step S12).

Finally, the display unit 4 displays the resistance component "$R_B$" and the reactance component "$X_B$" of the true impedance of the living body 5 as derived by the living body impedance calculation unit 20 (at step S13). Then, a sequence of process steps is terminated.

As described above, the living body impedance measurement apparatus according to the present invention is configured to measure the voltage attributed to the impedance of the targets (the living body or the external reference unit or the internal reference unit) by the measurement unit and to separate it into the voltage attributed to resistance component and the voltage attributed to reactance component by the separation unit based on hardware or software means. Accordingly, the resistance component intimately related to any impedance change factors is separated from the reactance component. Then, the fluctuation constant calculation unit is operated to substitute the voltage attributed to resistance component and the voltage attributed to reactance component as well as the resistance component and reactance component of the impedance of the external reference unit for terms in the impedance calculation formula (1) that takes into account of any impedance fluctuation and that is stored in the calculation formula storage unit in advance. As the result, the fluctuation constant is calculated, that is the constant for a fluctuation variable representing any fluctuation which may be caused due to impedance change factors. That is to say, any fluctuation which may be caused due to impedance change factors can clearly be represented by the numerical value. Furthermore, the living body impedance calculation unit calculates the resistance component and the reactance component of the true impedance of the living body by additionally substituting the fluctuation constant and the measured living body impedance for the terms in the impedance calculation formula (1) stored in the calculation formula storage unit in advance. Therefore, it is possible to provide the precise data for which any fluctuation due to impedance change factors is compensated.

In the embodiments as described above, the measurement has been performed using two external reference units: one has the known impedance (e.g. R=100 Ω, X=0 Ω) corresponding to the lower limit of the living body impedance measurement range; and the other has the known impedance (e.g. R=800 Ω, X=0 Ω) corresponding to the upper limit of the living body impedance measurement range. However, the present invention may be embodied by using a single and same external reference unit.

The measurement unit has been described as having the internal reference unit. However, in another embodiment, the measurement unit may have no such internal reference unit. It is noted, here, that the measurement unit having the internal reference unit, as shown in the above-mentioned embodiments, takes an advantage of the impedance measurement method as disclosed in Japanese Patent No. 2835656. That is to say, the measurement unit has less effect on the measurement by any fluctuation which may be caused due to any change in circumstances for the constant current source.

Furthermore, in the above-mentioned embodiments, the resistance component "$R_B$" and the reactance component "$X_B$" of the true impedance of the living body have individually been calculated and outputted at step S12. However, they may be output together as the true living body impedance consisting of the resistance component "$R_B$" and the reactance component "$X_B$".

Moreover, in the above-mentioned embodiments, the formula (1) derived from the circuit model in FIG. 2 has been used. However, the same advantage is attainable by deriving and using any one of the following formulae (2), (3), (4) and (5):

$$\begin{pmatrix} R_B \\ X_B \end{pmatrix} = \begin{pmatrix} C_R \\ C_X \end{pmatrix} \times \frac{\begin{pmatrix} V_{BR} \\ V_{BX} \end{pmatrix} + \begin{pmatrix} V_{OSR} \\ V_{OSX} \end{pmatrix}}{\begin{pmatrix} V_{RR} \\ V_{RX} \end{pmatrix} + \begin{pmatrix} m_R \\ m_X \end{pmatrix}} \qquad (2)$$

$$\begin{pmatrix} R_B \\ X_B \end{pmatrix} = \begin{pmatrix} C_R \\ C_X \end{pmatrix} \times \frac{\begin{pmatrix} V_{BR} \\ V_{BX} \end{pmatrix} + \begin{pmatrix} V_{OSR} \\ V_{OSX} \end{pmatrix}}{\begin{pmatrix} V_{RR} \\ V_{RX} \end{pmatrix} - \begin{pmatrix} V_{OSR} \\ V_{OSX} \end{pmatrix}} \qquad (3)$$

$$\begin{pmatrix} R_B \\ X_B \end{pmatrix} = \begin{pmatrix} C_R \\ C_X \end{pmatrix} \times \frac{\begin{pmatrix} V_{BR} \\ V_{BX} \end{pmatrix}}{\begin{pmatrix} V_{RR} \\ V_{RX} \end{pmatrix}} + \begin{pmatrix} V_{OSR} \\ V_{OSX} \end{pmatrix} \qquad (4)$$

$$\begin{pmatrix} R_B \\ X_B \end{pmatrix} = \begin{pmatrix} C_R \\ C_X \end{pmatrix} \times \frac{\begin{pmatrix} V_{BR} \\ V_{BX} \end{pmatrix}}{\begin{pmatrix} V_{RR} \\ V_{RX} \end{pmatrix}} + \begin{pmatrix} m_R \\ m_X \end{pmatrix} \qquad (5)$$

where "$m_R$" and "$m_X$" are constant.

In the above-mentioned embodiments, the frequency of the measuring current is 50 kHz and the living body is measured through one measuring path. However, multi-frequency measuring currents may be used if the same compensation formula is used and adjustments are made and the value of each of the compensation coefficients is stored. Furthermore, the living body may be measured through a number of measuring paths.

It is apparent from the foregoing that a living body impedance measurement apparatus according to the present invention is configured to measure the voltage attributed to the impedance of the targets (a living body or an external reference unit or an internal reference unit) by a measurement unit and to separate it into the voltage attributed to resistance component and the voltage attributed to reactance component by means of a separation unit. Then, a fluctuation constant calculation unit is operated to substitute the voltage attributed to resistance component and the voltage attributed to reactance component as well as the resistance component and reactance component of the impedance of the external reference unit for terms in the impedance calculation formula (1) that takes into account of any impedance fluctuation and that is stored in a calculation formula storage unit in advance. As the result, the fluctuation constant is calculated, that is the constant for a fluctuation variable representing any fluctuation which may be caused due to impedance change factors. Furthermore, a living body impedance calculation unit calculates the resistance component and the reactance component of the true impedance of the living body by additionally substituting the fluctuation constant and the measured living body impedance for the terms in the impedance calculation formula (1) stored in the calculation formula storage unit in advance. Accordingly, the resistance component intimately related to any impedance change factors is separated from the reactance component, and any fluctuation which may be caused due to impedance change factors is clearly represented by the numerical value (or the constant). Therefore, it is possible to provide the precise data of true living body impedance (true resistance component and true reactance component of the living body) for which any fluctuation due to impedance change factors is compensated.

What is claimed is:

1. A living body impedance measurement apparatus, comprising:
   a voltage measurement unit;
   a separation unit;
   a calculation formula storage unit;
   a fluctuation constant calculation unit;
   a fluctuation constant storage unit; and
   a living body impedance calculation unit, wherein
   said voltage measurement unit measures a voltage attributed to an impedance of a living body or an external reference unit, or of a living body, an external reference unit or an internal reference unit,
   said separation unit separates the voltage attributed to the impedance as measured by said measurement unit into a voltage attributed to its resistance component and a voltage attributed to its reactance component, said calculation formula storage unit stores an impedance calculation formula therein in advance, said impedance calculation formula correlates a true impedance variable representing resistance component and reactance component of true impedance of the living body or the external reference unit with a fluctuation variable representing a fluctuation which may be caused in said voltage measurement unit due to any impedance change factor as well as a measured voltage variable representing the voltage attributed to resistance component and the voltage attributed to reactance component of an actually measured impedance, said fluctuation constant calculation unit calculates a fluctuation constant that is the constant for the fluctuation variable by substituting the voltage attributed to resistance component and the voltage attributed to reactance component, which are separated from each other by said separation unit, corresponding to the voltage attributed to the impedance of the external reference unit as measured by the voltage measurement unit, as well as the resistance component and the reactance component of the impedance of the external reference unit as measured by the voltage measurement unit for terms in said impedance calculation formula stored in said calculation formula storage unit in advance, said fluctuation constant storage unit stores the fluctuation constant calculated by said fluctuation constant calculation unit, and said living body impedance calculation unit calculates the resistance component and the reactance component of the true living body impedance by substituting the fluctuation constant stored in the fluctuation constant storage unit and the voltage attributed to the living body impedance as measured by the voltage measurement unit for the terms in said impedance calculation formula stored in said calculation formula storage unit in advance.

2. A living body impedance measurement apparatus according to claim 1 wherein said fluctuation constant calculation unit calculates a fluctuation constant that is the constant for the fluctuation variable by substituting each voltage attributed to each resistance component and each voltage attributed to each reactance component, which are separated from each other by said separation unit, corresponding to each voltage attributed to each impedance of each of a plurality of different external reference units as measured by the voltage measurement unit, as well as each resistance component and each reactance component of each impedance of each of a plurality of different external reference units as measured by the voltage measurement unit for the terms in said impedance calculation formula stored in said calculation formula storage unit in advance.

3. A living body impedance measurement apparatus according to claim 2 wherein said impedance calculation formula includes:

fluctuation variables: "$C_R$" representing any fluctuation based on the scale factor and the phase of resistance component; "$C_X$" representing any fluctuation based on the scale factor and the phase of reactance component; "$V_{OSR}$" representing any fluctuation based on the offset voltage to resistance component axis; and "$V_{OSX}$" representing any fluctuation based on the offset voltage to reactance component axis;

measured voltage variables: "$V_{BR}$" representing the voltage attributed to resistance component of the living body or the external reference unit; "$V_{BX}$" representing the voltage attributed to reactance component; "$V_{RR}$" representing the voltage attributed to resistance component of the internal reference unit; and "$V_{RX}$" representing the voltage attributed to reactance component; and true impedance component variables: "$R_B$" representing resistance component of the true impedance of the living body or the external reference unit; and "$X_B$" representing reactance component of that true impedance, and said impedance calculation formula is written as follows:

$$\begin{pmatrix} R_B \\ X_B \end{pmatrix} = \begin{pmatrix} C_R \\ C_X \end{pmatrix} \times \frac{\begin{pmatrix} V_{BR} \\ V_{BX} \end{pmatrix} - \begin{pmatrix} V_{OSR} \\ V_{OSX} \end{pmatrix}}{\begin{pmatrix} V_{RR} \\ V_{RX} \end{pmatrix} - \begin{pmatrix} V_{OSR} \\ V_{OSX} \end{pmatrix}}.$$

* * * * *